United States Patent
Clark et al.

(10) Patent No.: US 8,124,167 B2
(45) Date of Patent: Feb. 28, 2012

(54) MEDICAL DEVICE WITH ADHERENT COATING, AND METHOD FOR PREPARING SAME

(75) Inventors: Tamisha Clark, Pfafftown, NC (US); Barry H. Chilton, Mt. Airy, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/732,786

(22) Filed: Mar. 26, 2010

(65) Prior Publication Data
US 2010/0200542 A1   Aug. 12, 2010

Related U.S. Application Data

(62) Division of application No. 10/783,910, filed on Feb. 20, 2004, now Pat. No. 7,687,144.

(60) Provisional application No. 60/448,778, filed on Feb. 20, 2003.

(51) Int. Cl.
*A61L 33/00* (2006.01)

(52) U.S. Cl. ........ 427/2.1; 117/47; 427/508; 427/385.5; 427/512; 427/521; 427/557; 427/559; 427/595; 427/316; 607/61; 428/375; 428/394; 428/395

(58) Field of Classification Search ............ 29/570; 427/508, 385.5, 512, 521, 557, 559, 595, 427/2.1; 117/47; 216/56; 607/61; 428/290
See application file for complete search history.

(56) References Cited

U.S. PATENT DOCUMENTS

| | | | |
|---|---|---|---|
| 3,632,387 A | * | 1/1972 | Sutherland .................. 427/307 |
| 3,735,480 A | * | 5/1973 | Yeamans .................... 29/25.03 |
| 3,990,381 A | | 11/1976 | Shepherd et al. |
| 4,459,318 A | | 7/1984 | Hyans |
| 4,744,857 A | | 5/1988 | Nelson |
| 4,842,889 A | | 6/1989 | Hu et al. |
| 5,001,009 A | | 3/1991 | Whitbourne et al. |
| 5,084,022 A | | 1/1992 | Claude |
| 5,238,004 A | | 8/1993 | Sahatjian et al. |
| 5,331,027 A | | 7/1994 | Whitbourne et al. |
| 5,427,831 A | | 6/1995 | Stevens |
| 5,772,609 A | | 6/1998 | Nguyen et al. |
| 5,932,299 A | * | 8/1999 | Katoot .................... 427/508 |

(Continued)

FOREIGN PATENT DOCUMENTS

EP  0405823  1/1991

(Continued)

OTHER PUBLICATIONS

ABB Etching Service Company, LLC, "Commonly Asked Quetins" [online]. Available from http://www.abbetch.com/faq.htm [accessed Feb. 20, 2003].

(Continued)

*Primary Examiner* — Dah-Wei Yuan
*Assistant Examiner* — Andrew Bowman
(74) *Attorney, Agent, or Firm* — Woodard, Emhardt, Moriarty, McNett & Henry LLP

(57) ABSTRACT

A medical device such as a wire guide has a lubricious and/or therapeutic coating adhered to an etched, carbonaceous polymeric surface, for example a sodium-etched polymer surface. A method for preparing a lubricious and/or therapeutic coating on a medical device includes etching a polymeric portion of the device to create a carbonaceous surface and applying a lubricious and/or therapeutic coating on the etched surface.

17 Claims, 1 Drawing Sheet

U.S. PATENT DOCUMENTS

| | | |
|---|---|---|
| 6,059,738 A | 5/2000 | Stoltze et al. |
| 6,139,510 A | 10/2000 | Palermo |
| 6,159,187 A | 12/2000 | Park et al. |
| 6,203,505 B1 | 3/2001 | Jalisi et al. |
| 6,432,510 B1 | 8/2002 | Kim et al. |
| 6,569,107 B2 | 5/2003 | Jalisi et al. |
| 6,861,006 B2 * | 3/2005 | Ferain et al. .................. 216/56 |
| 2001/0003146 A1 | 6/2001 | Jalisi et al. |
| 2004/0167442 A1 | 8/2004 | Shireman et al. |
| 2004/0167443 A1 | 8/2004 | Shireman et al. |
| 2005/0027214 A1 | 2/2005 | Murayama et al. |
| 2005/0054952 A1 | 3/2005 | Eskuri et al. |
| 2005/0145307 A1 | 7/2005 | Shireman et al. |
| 2005/0232965 A1 | 10/2005 | Falotico |
| 2006/0047224 A1 | 3/2006 | Grandfield |
| 2006/0073264 A1 | 4/2006 | Sakane et al. |

FOREIGN PATENT DOCUMENTS

| | | |
|---|---|---|
| WO | WO 92/07464 | 5/1992 |
| WO | WO 00/74565 | 12/2000 |

OTHER PUBLICATIONS

STS Biopolymers, Inc., an SIS company, SLIP-COAT Antimicrobial and/or Antithrombogenic Agents Technical Bulletin, Bulleting 6B, Aug. 1996.

* cited by examiner

MEDICAL DEVICE WITH ADHERENT COATING, AND METHOD FOR PREPARING SAME

REFERENCE TO RELATED APPLICATION

The present application is a divisional patent application of U.S. patent application Ser. No. 10/783,910 filed Feb. 20, 2004, now U.S. Pat. No. 7,687,144, which claims the benefit of U.S. Provisional Patent Application Ser. No. 60/448,778, filed Feb. 20, 2003, both entitled MEDICAL DEVICE WITH ADHERENT COATING, AND METHOD FOR PREPARING SAME, and both of which are hereby incorporated by reference in their entirety.

BACKGROUND OF THE INVENTION

This invention relates generally to medical devices, and more particularly to elongate medical devices useful in minimally invasive procedures, such as wire guides and related devices.

Medical devices such as wire guides are often coated with another material, for example to increase the lubricity of a surface or to serve as a carrier for release of a therapeutic substance. A number of different coating strategies have been suggested and employed, including strategies that involve covalent, ionic, or hydrogen bonding of the material to the device surface.

Difficulties arise in that the coating material and the device surface sometimes do not adhere to one another to provide sufficient integrity to the coating. This is particularly a problem when non-covalent bonding of the coating material is involved. This is also a particular problem when the device surface is formed with a material, such as a fluoropolymer, that is chosen for its inert, non-reactive, non-adherent qualities.

The present invention is addressed to these problems.

SUMMARY OF THE INVENTION

The present invention provides in one embodiment an elongate medical device, such as a wire guide, having a fluoropolymer surface, and a lubricious and/or therapeutic coating stably adhered to the fluoropolymer surface. In preferred devices the coating is a lubricious coating and/or the fluoropolymer surface has been modified to form a carbonaceous film, for example using a strong chemical etchant such as metallic sodium.

In another embodiment, the present invention provides a medical device comprising an elongate member for traversing a bodily passage, the elongate member having an etched carbonaceous surface; and, a lubricious and/or therapeutic coating on said surface.

In another embodiment, the present invention provides a medical device, comprising a member for traversing or implantation within a bodily passage, the member including a polymer portion having an etched carbonaceous surface. The device also has a lubricious and/or therapeutic coating adhered to the etched surface.

The invention provides in another embodiment a medical device comprising a polymer surface, the polymer surface having been treated to remove atoms and increase the hydrophilic character of the surface. A lubricious and/or therapeutic coating is adhered to the treated polymer surface. Preferred medical devices include wire guides, catheters, and stents.

The present invention also provides a method for applying a lubricious coating to a medical device, comprising providing a medical device having a sodium-etched polymer surface, and applying a lubricious and/or therapeutic coating to the etched surface.

Another embodiment of the invention provides a method for manufacturing a medical wire guide, comprising the steps of (a) providing an elongate wire; (b) applying a polymer coating on the elongate wire; (c) etching the polymer coating with sodium metal to form an etched polymer surface; and (d) applying a lubricious and/or therapeutic coating on the etched polymer surface.

Still another embodiment of the invention provides a method for applying a lubricious and/or therapeutic coating to a medical device. The method includes the step of applying a lubricous and/or therapeutic coating to an etched carbonaceous surface on a polymeric portion of the medical device.

Additional embodiments as well as features and advantages of the invention will be apparent from the descriptions herein.

DESCRIPTION OF THE PREFERRED EMBODIMENT

Figure 1:
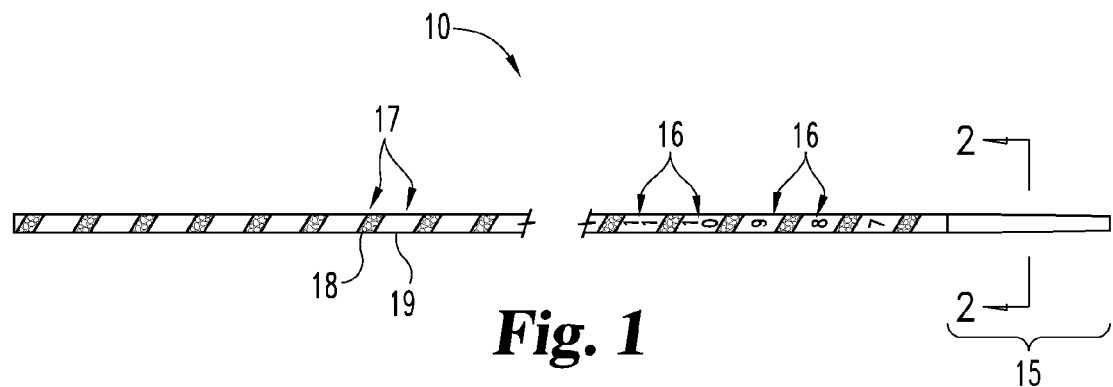
FIG. 1 depicts a side view of an illustrative wire guide embodiment of the present invention.
Figure 2:
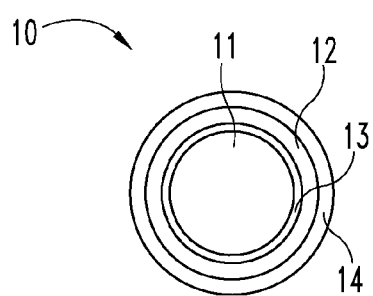
FIG. 2 depicts a cross-sectional view of the wire guide of FIG. 1 taken along line 2-2 and viewed in the direction of the arrows.

For the purpose of promoting an understanding of the principles of the present invention, reference will now be made to the embodiment illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein are contemplated as would normally occur to one skilled in the art to which the invention relates.

With reference to FIG. 1, a medical wire guide 10 or similar elongate device for traversing bodily passages is provided. The illustrative device 10 preferably comprises a standard exchange wire guide, e. g., 480 cm or 260 cm in length, with a solid core wire 11, formed from a metal such as nitinol, and a coating 12 on the wire 11, comprising a polymer such as a fluoropolymer, e.g. polytetrafluoroethylene (PTFE), that is shrink-wrapped over the wire. It will be understood that the present invention also applies to wire guide devices having outer surface coatings applied in other manners such as dipping, extruding over or otherwise coating the internal core wire 11.

The preferred device 10 also includes a distal portion having a radioactive marker material 13, either as a single marker, a plurality of markers, or an extended radiopaque region that is several centimeters long (e.g., the distal 5 cm). Methods of providing radiopacity include standard techniques such as the addition of a distal platinum coil, adding gold or other radiopaque material markers, using radiopaque inks, or the use of radiopaque shrink wrap or tubing over the core wire, e.g., radiopaque urethane, or dipping the wire in a radiopaque polymer, or affixing a polymer tip, such as PEBAX, that has been loaded with radiopaque powder, such as tungsten.

The device 10 may also have a lubricious coating 14 applied upon a distal tip portion. The lubricious coating 14 provides lubricity while the device 10 traverses a body passageway to ease the use of the device and prevent damage to tissues lining the passageway. The lubricious coating 14 is applied overtop a portion of the polymer coating 12 that has been modified to improve the adherence of the lubricious coating 14. In accordance with the invention, such modifications will typically involve the abstraction and replacement of atoms or chemical groups presented at the surface of the polymer coating 12 in a manner that increases the level of adherence of the lubricious coating 14. These modifications may, for example, also be evidenced by an increase in the wettability and/or hydrophilic character of the surface of the polymer coating 12. Illustratively, the surface modification may involve the removal of atoms or chemical groups from the polymer coating material and the formation of a carbonaceous film or surface that is more adherent to the polymer(s) used in the lubricious coating than the corresponding unmodified polymer surface. For instance, where a fluoropolymer coating 12 is present, the surface modification may involve the removal of fluorine atoms and the formation of a carbonaceous surface. Removal of atoms such as fluorine atoms may be accomplished utilizing strong chemical etchants such as metallic sodium, as occurs for example in products comprising sodium-naphthalene complexes (e.g. FluroEtch® Safety Solvent, Acton Technologies, Inc., Pittston, Pa., USA). The resulting carbonaceous film presents a surface-exposed carbonaceous backbone that typically includes relatively polar organic groups, including oxygen-containing organic groups such as hydroxyl groups and carbonyl-containing groups. In such etching processes, the etchant can be contacted one or more times with the polymer coating 12 in any suitable manner, including dipping, spraying, and the like. In a dipping process, a fluoropolymer coating 12 can be suitably contacted with a sodium metal etchant for a period sufficient to form the carbonaceous film, for example up to about 5 minutes or more, and typically about 30 seconds to about 5 minutes. Thereafter, the etched surface is desirably rinsed thoroughly, for example with an alcohol and/or warm water, prior to the application of coating(s) thereon.

A wide variety of lubricious coating materials may be used for purposes of coating the etched surface. Preferred materials are disclosed in U.S. Pat. Nos. 5,001,009 and 5,331,027 to Whitbourne et al., and commercially available from STS Biopolymers, Inc. of Henrietta, N.Y., USA, under the tradename SLIP-COAT®. More preferred are coatings including an overlying layer containing a relatively hydrophilic lubricious polymer and an underlying layer containing a relatively less hydrophilic and less lubricious coating material. The hydrophilic polymer is a polyolefin such as a vinyl polymer having polar pendant groups, a polyacrylate or methacrylate having hydrophilic esterifying groups, a polyether, a polyethylene glycol, or other polyolefin with hydrophilic characteristics. The hydrophilic polymer is preferably polyvinylpyrrolidone or polyvinylpyrrolidone vinyl acetate. The underlying or "basecoat" polymer is advantageously a water-insoluble polymer that does not significantly react with the hydrophilic polymer in solution, and is preferably cellulose ester, a copolymer of polymethyl vinyl ether and maleic anhydride, or nylon. Cellulose esters are most preferred, including for example ethyl cellulose, hydroxyethyl cellulose, cellulose nitrate, cellulose acetate, cellulose acetate butyrate, and cellulose acetate proprionate. Preferably, the basecoat polymer and hydrophilic top coat polymer are applied in separate steps, with drying after each step at a suitable temperature usually ranging from about 50° F. to about 150° F., although higher or lower temperatures may also be used.

The coating 14 may also serve one or more therapeutic purposes, by incorporating one or more therapeutic agents, for example antibiotic(s) and/or anti-thrombogenic agent(s), for release during the residence of device 10 within the body. In this regard, coating 14 may possess either or both of lubricious and therapeutic properties, and given the teachings herein it is within the purview of those skilled in the art to select appropriate coating materials for these purposes.

Device 10 may also include a pigmented portion 15 along the distal-most portion of the wire. The pigmented portion 15 of the distal tip may, for example, be a solidly pigmented portion that coincides with the span of the underlying coil or other radiopaque material, and provides both a reference nearing the end of the wire, and an endoscopically visible reference that can be positionally compared to a radiographic image of the coil or other radiopaque material. Any suitable pigment may be used for pigmented portion 15, either applied overtop the polymer coating 12 or incorporated therein, or both. In addition, polymer coating 12 in areas at the distal tip of device 10 may be formed from the same polymer as, or a different polymer from, the polymer coating on the remainder of the device 10. Where a PTFE polymer coating 12 is used, a compatible PTFE (e.g. Teflon®) pigment may be used. Any suitable pigment may be used, including both colors and hues such as black, gray or white pigments. A variety of suitable PTFE pigments are commercially available, including for example Black Striping Ink sold by GEM Gravure Company, Inc., West Hanover, Mass., USA. Where a polymer-based ink such as a fluoropolymer (e.g. PTFE) ink is used, the ink coating may serve as the polymer surface or coating to be etched in accordance with the present invention. Excellent adherence of and cohesiveness of the lubricious and/or therapeutic coating 14 can be achieved using non-covalent interactions such as ionic and/or hydrogen bonding and potentially also molecular intermixing of the polymers. Thus, lubricious and/or therapeutic coatings 14 of the invention may lack covalent bonding to the polymer coating 12 or between multiple layers (if present) of the coating 14, for example incorporating film-forming polymers. If desired, however, reactive monomers or other reactive functional groups could be introduced to induce covalent bonding to the polymer coating 12 and/or between layers of the lubricious and/or therapeutic coating 14.

In a preferred wire guide manufacturing process, a platinum coilspring is welded onto the distal, tapered tip of a nitinol core wire. The nitinol core wire is inserted into a PTFE sheath bearing spiral indicia, distal end first, and the sheath is heat shrunk to the wire using conventional techniques. After trimming any excess sheath material, a PTFE black striping ink (Gem Gravure) is applied to the distal tip by dipping into the ink and drying at an elevated temperature of about 1000° F. The ends of the wire are conventionally closed, and the wires are grit-blast roughened over approximately 5 cm of the distal tip. The roughened 5 cm of the distal tip are dipped into the sodium etchant, and rinsed well, for example with warm water and/or a polar organic solvent such as an alcohol (e.g. isopropanol) and/or acetone. After drying, a film-forming, two-coat SLIP-COAT® system is then used to form a lubricious coating on the distal 5 cm of the wire by first applying a cellulose ester basecoat (e.g. ethyl cellulose, hydroxyethyl cellulose, cellulose nitrate, cellulose acetate, cellulose acetate butyrate, or cellulose acetate proprionate, and potentially also containing the ink) and drying at a temperature of about 110° F. for about 5 minutes, and then applying the hydrophilic polyvinylpyrrolidone top coat overtop the basecoat and again drying at a temperature of about 100° F. for about an hour. The resulting coating is highly coherent and stably adhered to the wire.

Medical devices such as wire guides of the invention can also have the features disclosed in International Application Serial No. PCT/US00/15532 filed Jun. 5, 2000 and published as WO 00/74565 on Dec. 14, 2000, which is hereby incorporated herein by reference in its entirety. Thus, wire guide 10 may be an exchange wire guide adapted for use with an endoscope, having multiple types of indicia for indicating position and/or movement within a body of a patient. For example, as illustrated in FIG. 1, the wire guide can include an indicia pattern that is at least partially visible by direct or endoscopic observation. The indicia pattern comprises a first system of indicia 16 and a second system of indicia 17. The first system of indicia includes series of scale reference markings that uniquely identify the particular distance to a fixed reference point on the elongate member, such as the distal tip. These scale references markings can include numerals (as shown in FIG. 1), differently numbered bands, dots, etc., or some other form of unique indicia. The second system of indicia 17 is imprinted on, or incorporated into the elongate member to allow the endoscopist or operator to readily determine whether the elongate member is moving relative to the endoscope into which it situated. The second system of indicia can comprise helical strips 18 and 19 (FIG. 1) containing two different colors or alternatively oblique lines, helical stripes, closely placed marking, or another pattern of indicia that allow one to detect longitudinal shifts in position by viewing the device through an endoscope or monitoring the external portion of the elongate member that extends proximally from the endoscope. Various embodiments of use of the second system of indicia 17 include placement of oblique or closely spaced markings on the distal portion to be viewed by the endoscope, placement of the markings at the proximal portion of the elongate member such that they can be directly viewed externally of the patient to determine relative movement, or to incorporate the helical pattern into the device, e.g., providing a striped wire guide coating or co-extrusion of a bicolor catheter. In the case of the latter, the printed scale reference marker, bands, oblique lines, etc. can be printed over the surface of the device having the helical pattern.

Coated medical devices of the invention may include, for example, exchange wire guides as disclosed above for use in the gastrointestinal tract, vascular wire guides, catheters, stents such as plastic drainage stents for the gastrointestinal system (e.g. fabricated from PTFE, polyurethane or polyethylene), or other medical devices potentially benefiting from lubricious and/or therapeutic coatings, particularly medical devices for traversal of or implantation within bodily passages. Such devices present polymeric surfaces that can be modified and coated with lubricious and/or therapeutic coatings as disclosed above.

While the invention has been described in detail above with reference to specific embodiments, it will be understood that modifications and alterations in the embodiments disclosed may be made by those practiced in the art without departing from the spirit and scope of the invention. All such modifications and alterations are intended to be covered. In addition, all publications cited herein are indicative of the abilities of those of ordinary skill in the art and are hereby incorporated by reference in their entirety as if each had been individually incorporated by reference and fully set forth.

What is claimed is:

1. A method for applying a lubricious and/or therapeutic coating to a medical device, comprising applying a lubricous and/or therapeutic coating to a sodium etched carbonaceous surface of a polymeric portion of the device, wherein said lubricious and/or therapeutic coating comprises an antibiotic or anti-thrombogenic agent.

2. The method of claim 1, wherein the polymer is a fluoropolymer.

3. The method of claim 2, wherein the fluoropolymer is polytetrafluoroethylene.

4. The method of claim 1, wherein the medical device is a wire guide, catheter, or stent.

5. The method of claim 4, wherein the medical device is a wire guide.

6. The method of claim 1, which comprises applying said lubricious coating, wherein said lubricious coating comprises one or more polymers non-covalently adhered to the polymer surface.

7. The method of claim 6, wherein said lubricous coating comprises polyvinylpyrrolidone or a copolymer thereof.

8. A method for manufacturing a medical wire guide, comprising:
   providing an elongate wire;
   applying a fluoropolymer coating on the elongate wire;
   etching the fluoropolymer coating with sodium metal to faun an etched fluoropolymer surface; and
   applying a lubricious coating to the etched fluoropolymer surface so as to provide to the device an overlying lubricious layer that provides lubricity to the device as the device traverses a body passageway;
   wherein the fluoropolymer is polytetrafluoroethylene; and
   wherein said lubricious coating comprises one or more polymers non-covalently adhered to the fluoropolymer surface.

9. The method of claim 8, wherein said lubricous coating comprises polyvinylpyrrolidone or a copolymer thereof.

10. A method for applying a lubricious and/or therapeutic coating to a medical device, comprising applying a lubricous and/or therapeutic coating to an etched carbonaceous surface of a polymeric portion of the device so as to provide to the device an overlying lubricious and/or therapeutic layer that provides lubricity to the device as the device traverses a body passageway and/or that incorporates a therapeutic agent for release within the body;
   wherein the etched carbonaceous surface has been sodium etched; and
   wherein said lubricious and/or therapeutic coating comprises an antibiotic or anti-thrombogenic agent.

11. The method of claim 10, wherein the polymeric portion comprises a fluoropolymer.

12. The method of claim 11, wherein the fluoropolymer is polytetrafluoroethylene.

13. The method of claim 10, wherein the medical device is a wire guide, catheter, or stent.

14. The method of claim 13, wherein the medical device is a wire guide.

15. The method of claim 10, wherein said lubricious and/or therapeutic coating comprises one or more film-forming polymers.

16. A method for manufacturing a medical wire guide, comprising:
   providing an elongate wire;
   applying a polytetrafluoroethylene coating on the elongate wire;
   etching the polytetrafluoroethylene coating with sodium metal to form an etched polytetrafluoroethylene surface; and
   applying a lubricious coating to the etched polytetrafluoroethylene surface, wherein the lubricous coating comprises one or more polymers non-covalently adhered to the polytetrafluoroethylene surface.

17. The method of claim 16, wherein said lubricous coating comprises polyvinylpyrrolidone or a copolymer thereof.

* * * * *